(12) United States Patent
Osypka

(10) Patent No.: US 9,913,684 B2
(45) Date of Patent: Mar. 13, 2018

(54) STEERABLE ABLATION CATHETER FOR RENAL DENERVATION

(71) Applicant: Oscor Inc., Palm Harbor, FL (US)

(72) Inventor: Thomas P. Osypka, Palm Harbor, FL (US)

(73) Assignee: Oscor Inc., Palm Harbor, FL (US)

( * ) Notice: Subject to any disclaimer, the term of this patent is extended or adjusted under 35 U.S.C. 154(b) by 290 days.

(21) Appl. No.: 14/454,978

(22) Filed: Aug. 8, 2014

(65) Prior Publication Data

US 2015/0057655 A1 Feb. 26, 2015

Related U.S. Application Data

(60) Provisional application No. 61/886,117, filed on Oct. 3, 2013, provisional application No. 61/869,140, filed on Aug. 23, 2013, provisional application No. 61/886,132, filed on Oct. 3, 2013.

(51) Int. Cl.
*A61B 18/14* (2006.01)
*A61B 17/00* (2006.01)
*A61B 18/00* (2006.01)

(52) U.S. Cl.
CPC .... *A61B 18/1492* (2013.01); *A61B 2017/003* (2013.01); *A61B 2018/00404* (2013.01); *A61B 2018/00434* (2013.01); *A61B 2018/00511* (2013.01); *A61B 2018/00577* (2013.01); *A61B 2018/00821* (2013.01); *A61B 2018/00916* (2013.01); *A61B 2018/1435* (2013.01); *A61B 2018/1467* (2013.01)

(58) Field of Classification Search
CPC ............ A61B 1/005; A61B 2018/1467; A61B 2018/00511; A61B 2018/1435
See application file for complete search history.

(56) References Cited

U.S. PATENT DOCUMENTS

| | | | |
|---|---|---|---|
| 5,215,540 A | 6/1993 | Anderhub | |
| 5,364,352 A * | 11/1994 | Cimino | A61B 5/0422 604/264 |
| 5,372,587 A | 12/1994 | Hammerslag et al. | |
| 5,456,664 A | 10/1995 | Heinzelman et al. | |

(Continued)

FOREIGN PATENT DOCUMENTS

| WO | WO-2012/075156 A1 | 6/2012 |
|---|---|---|
| WO | WO-2012/158864 A1 | 11/2012 |

OTHER PUBLICATIONS

European Search Report dated Nov. 7, 2014 issued on European Patent Application No. 14180667.9.

*Primary Examiner* — Joseph Stoklosa
*Assistant Examiner* — Tigist Demie
(74) *Attorney, Agent, or Firm* — Locke Lord LLP; Scott D. Wofsy

(57) ABSTRACT

A catheter for ablation of the interior walls of the renal artery includes an elongated catheter body having opposing proximal and distal end portions, a plurality of axially spaced apart electrodes aligned along the distal end portion of the catheter body, and a catheter handle at the proximal end portion of the catheter body including means for operatively connecting the handle to a generator, wherein energy from the generator is provided to the plurality of electrodes for ablation of the renal artery, wherein the handle is configured to steer the distal end portion of the catheter body in at least one direction.

13 Claims, 18 Drawing Sheets

(56) References Cited

U.S. PATENT DOCUMENTS

| | | | |
|---|---|---|---|
| 5,462,527 A * | 10/1995 | Stevens-Wright | A61B 18/1492 600/585 |
| 5,792,140 A * | 8/1998 | Tu | A61B 18/08 606/41 |
| 5,800,413 A | 9/1998 | Swartz et al. | |
| 5,827,227 A * | 10/1998 | DeLago | A61M 25/0662 604/104 |
| 5,893,885 A | 4/1999 | Webster, Jr. | |
| 6,004,280 A | 12/1999 | Buck et al. | |
| 6,146,355 A | 11/2000 | Biggs | |
| 7,232,422 B2 | 6/2007 | Gibson et al. | |
| 8,348,888 B2 | 1/2013 | Selkee | |
| D708,740 S | 7/2014 | Osypka et al. | |
| 2006/0030753 A1* | 2/2006 | Boutillette | A61B 1/00071 600/146 |
| 2006/0041295 A1* | 2/2006 | Osypka | A61N 1/0558 607/117 |
| 2007/0129747 A1* | 6/2007 | Dorman | A61B 17/02 606/191 |
| 2008/0097386 A1 | 4/2008 | Osypka | |
| 2009/0240235 A1* | 9/2009 | Murata | A61M 25/001 604/527 |
| 2010/0106141 A1 | 4/2010 | Osypka et al. | |
| 2010/0191151 A1* | 7/2010 | Kwak | A61B 18/1492 600/585 |
| 2011/0306851 A1 | 12/2011 | Wang | |
| 2012/0029510 A1 | 2/2012 | Haverkost | |
| 2012/0116383 A1* | 5/2012 | Mauch | A61B 18/1492 606/33 |

* cited by examiner

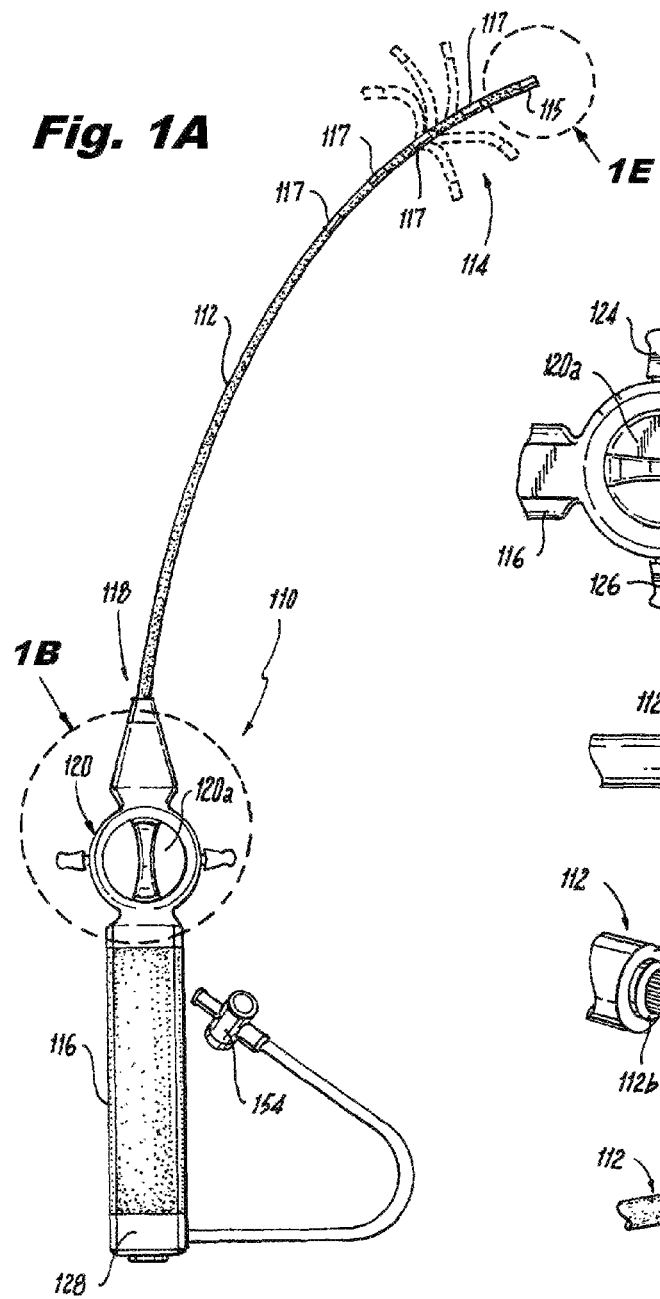
Fig. 1A
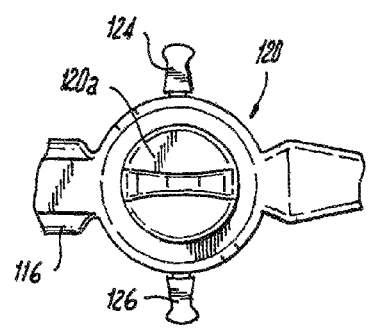
Fig. 1B
Fig. 1C
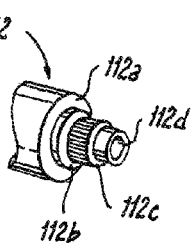
Fig. 1D
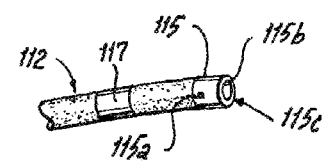
Fig. 1E

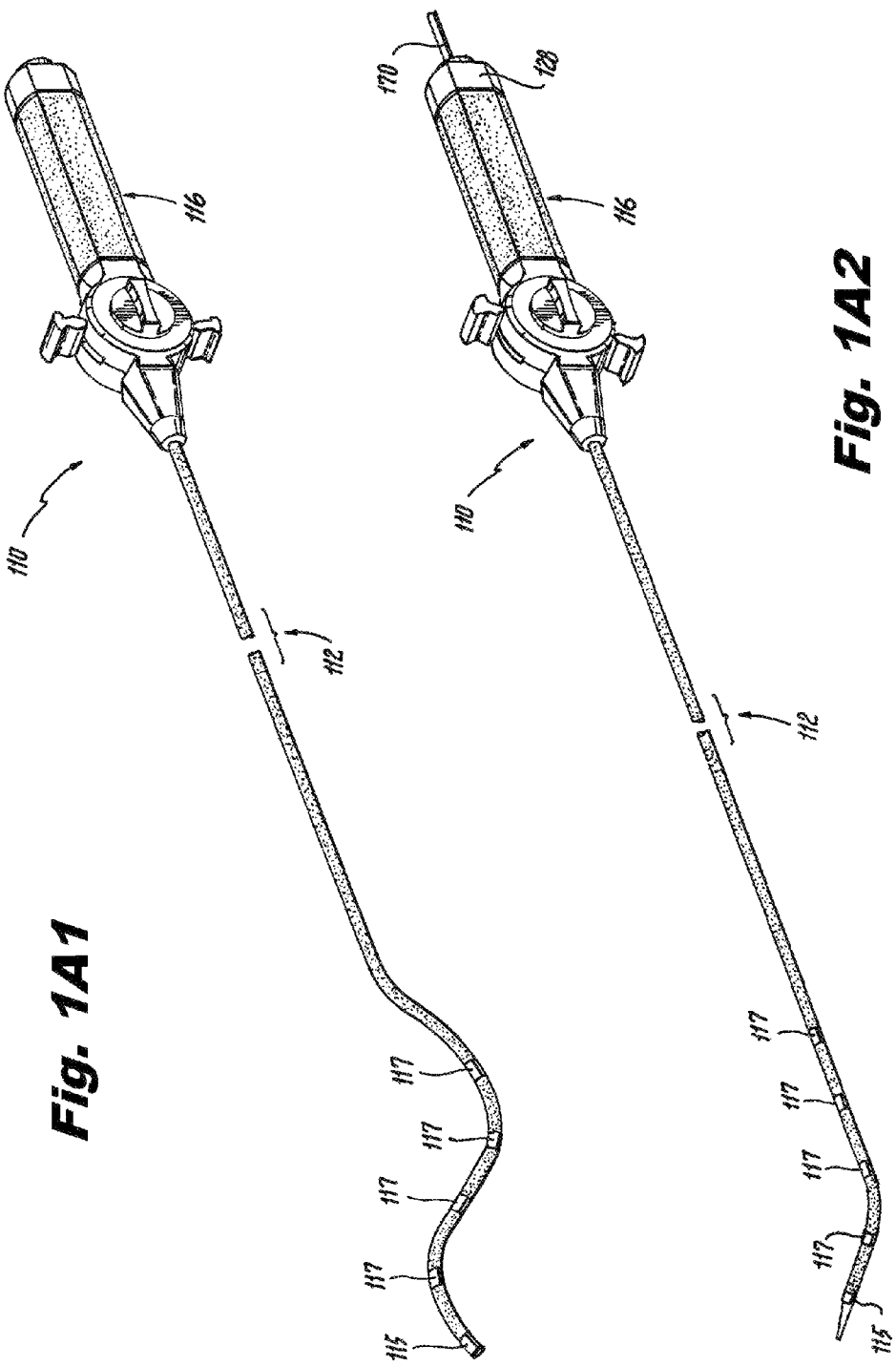

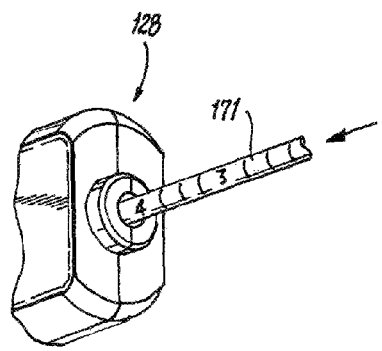
Fig. 1F
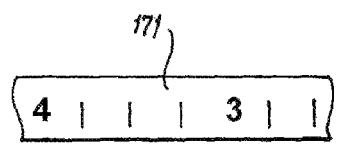
Fig. 1I
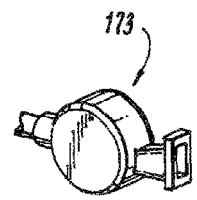
Fig. 1H
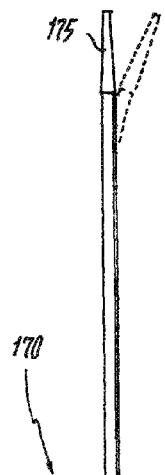
Fig. 1G
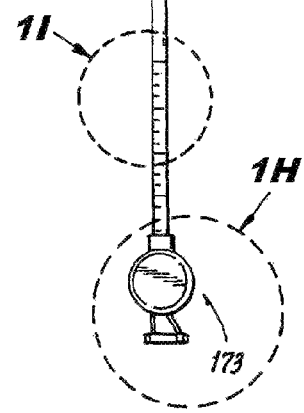

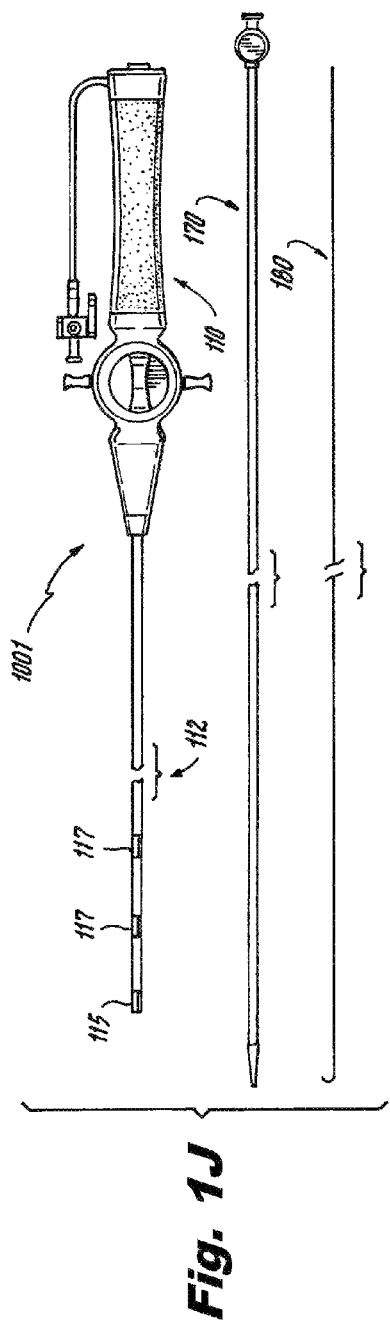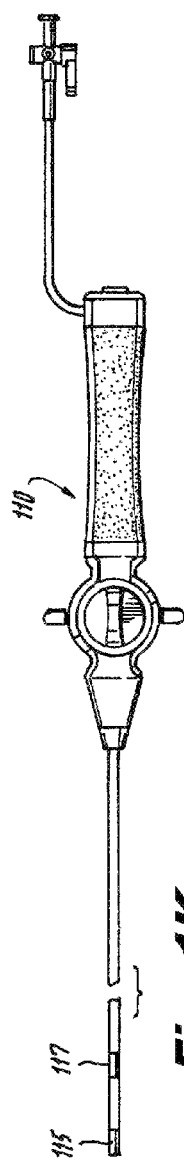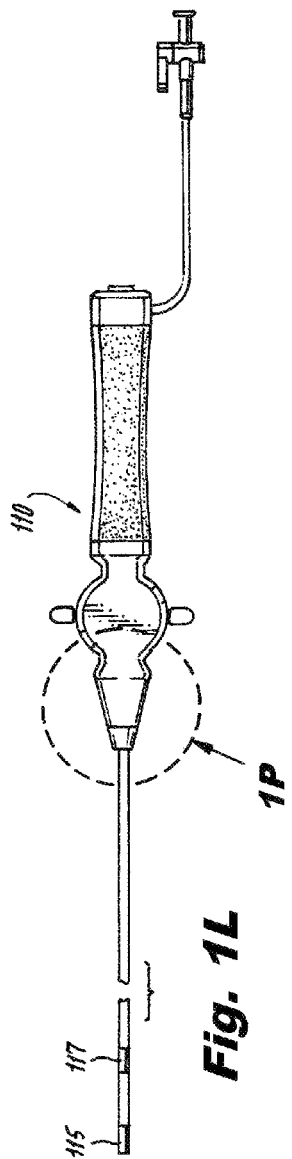
Fig. 1J
Fig. 1K
Fig. 1L

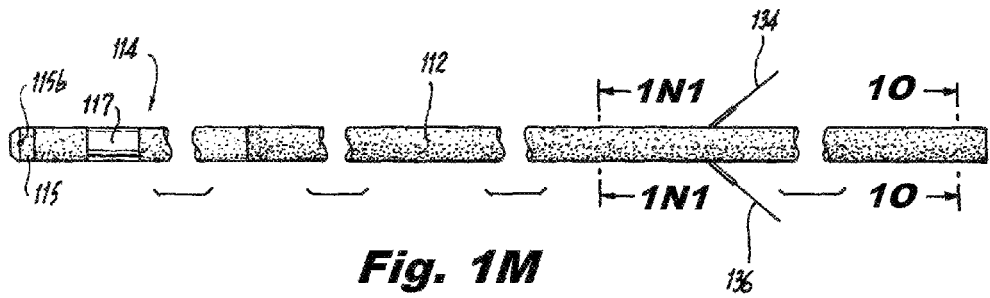
Fig. 1M
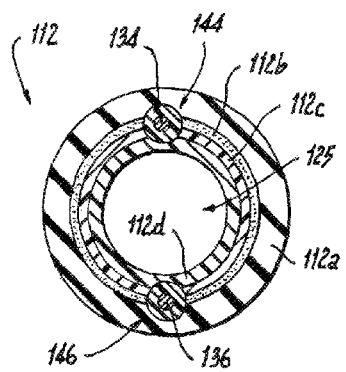
Fig. 1N1
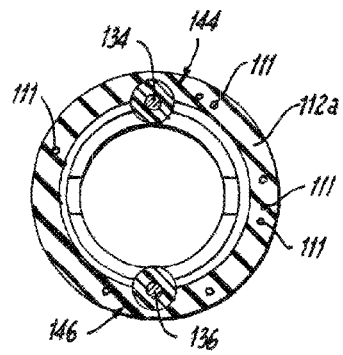
Fig. 1N2
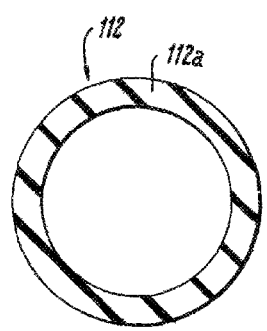
Fig. 1O
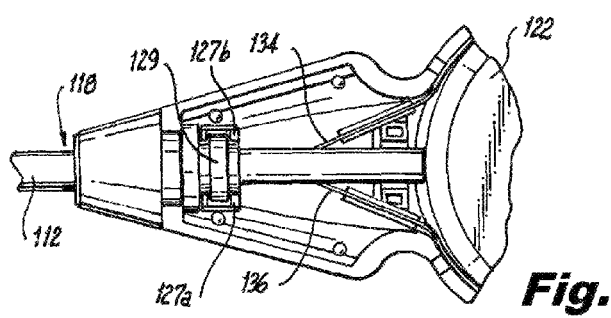
Fig. 1P

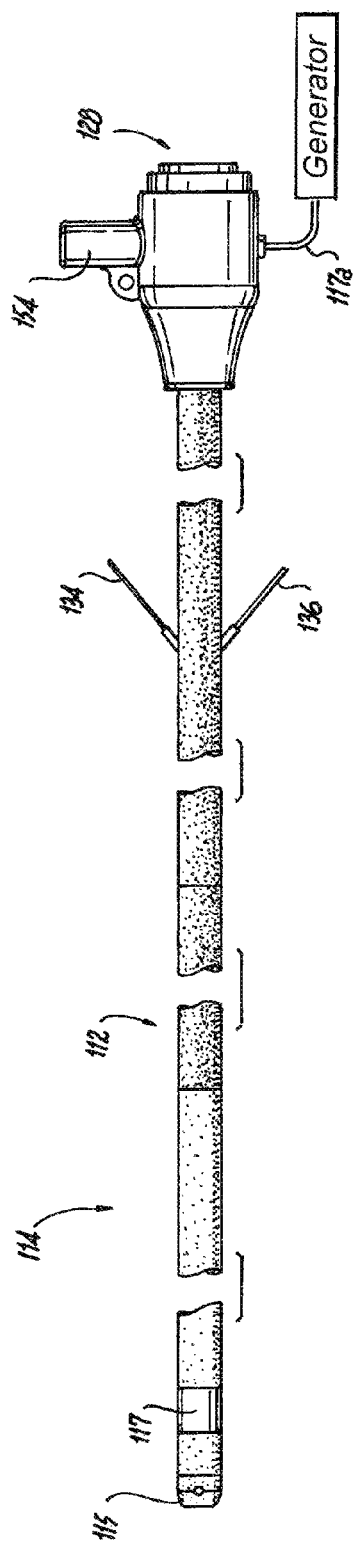
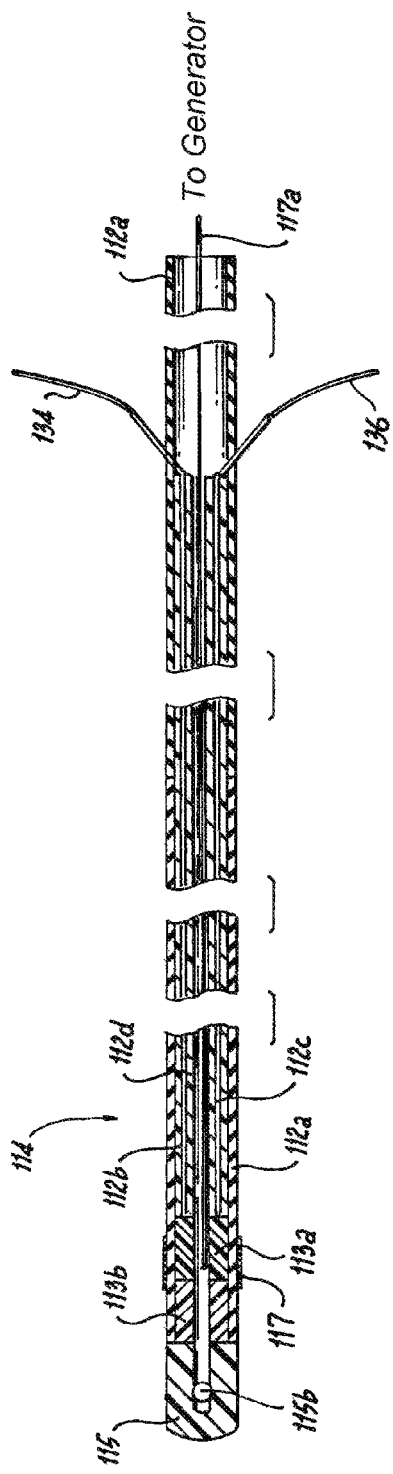
Fig. 1Q
Fig. 1R

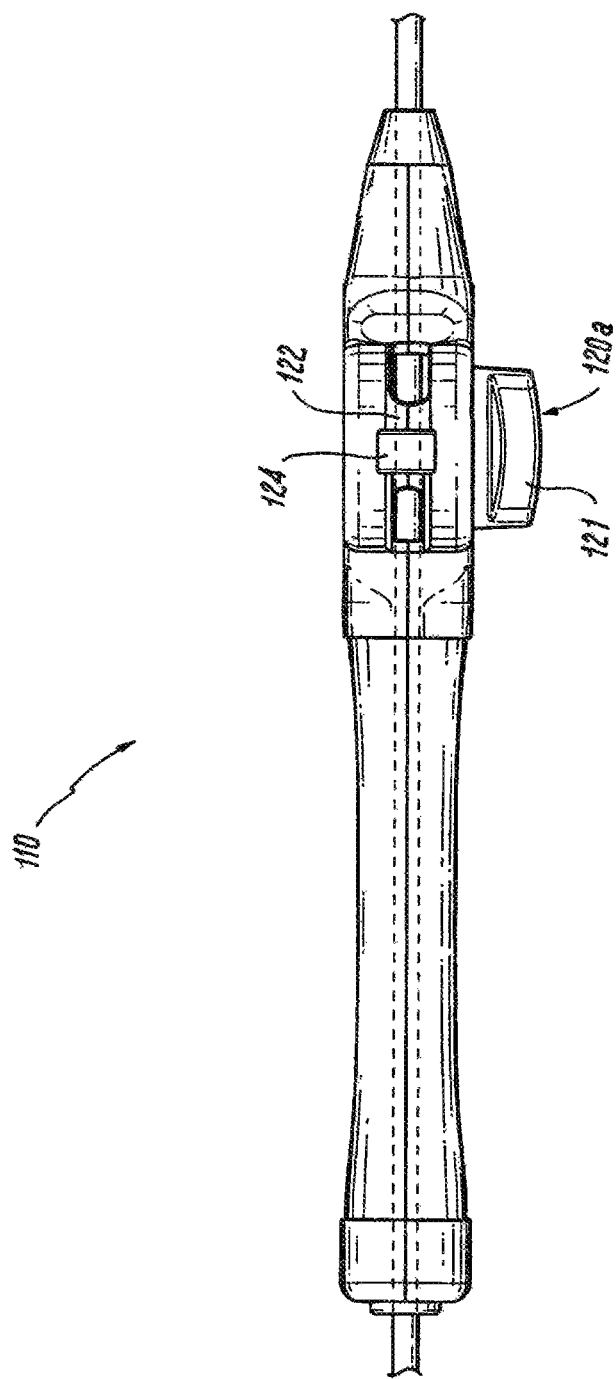

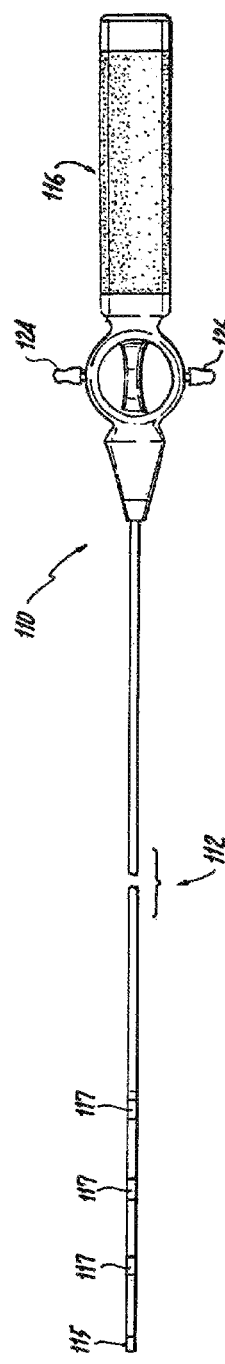
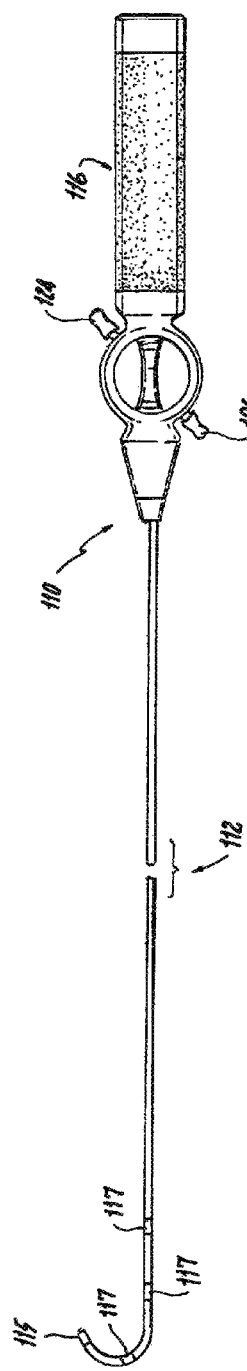
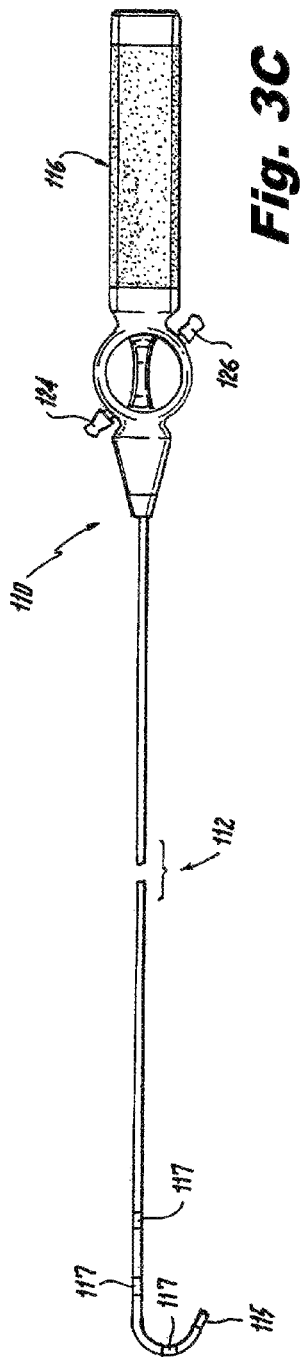

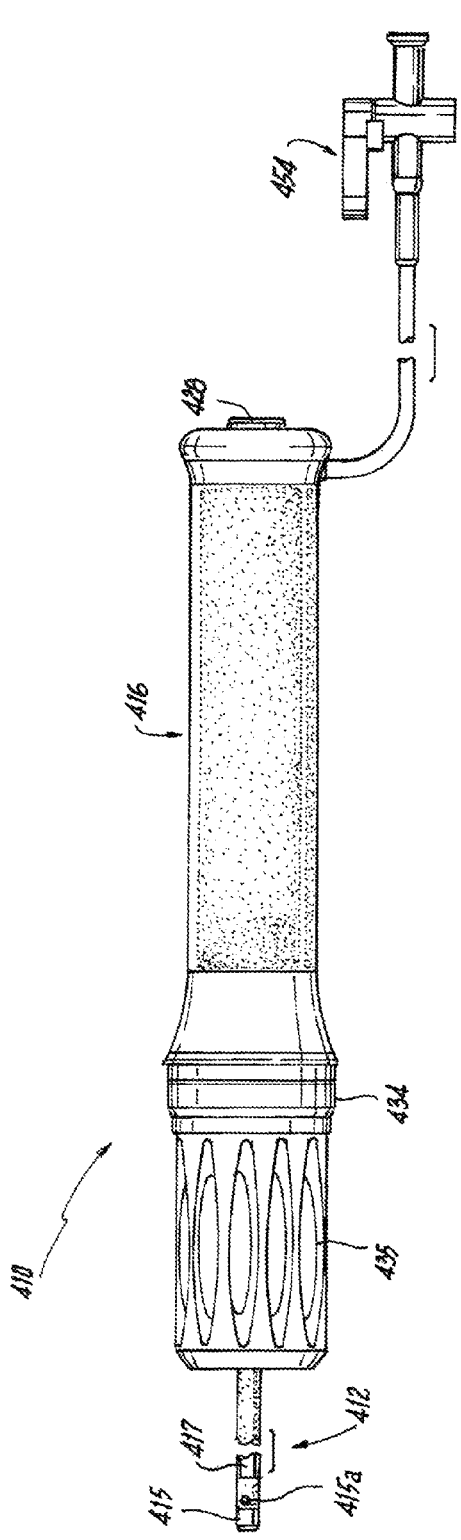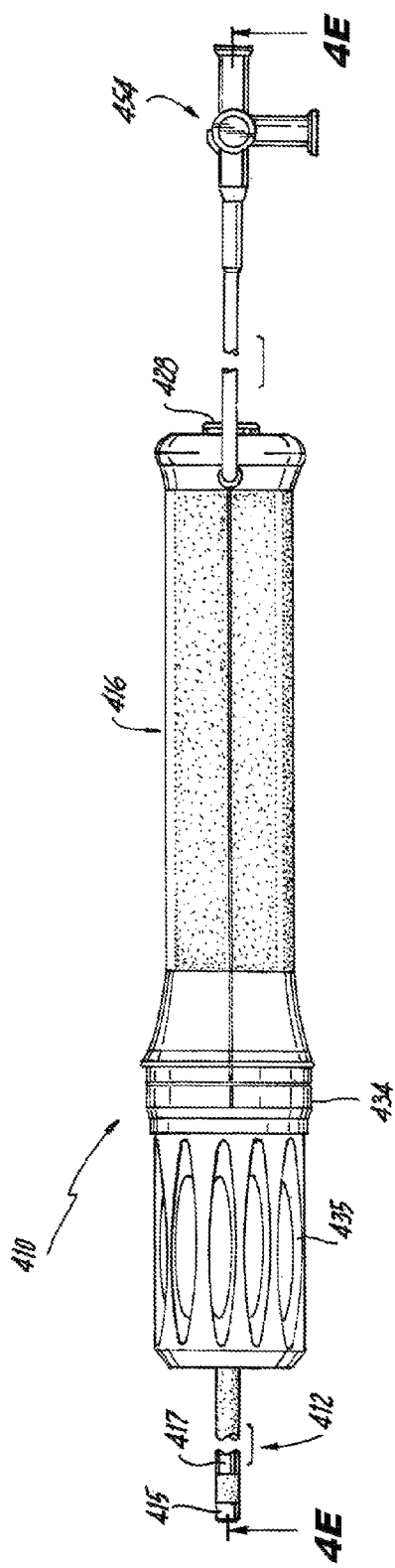
Fig. 4B
Fig. 4C

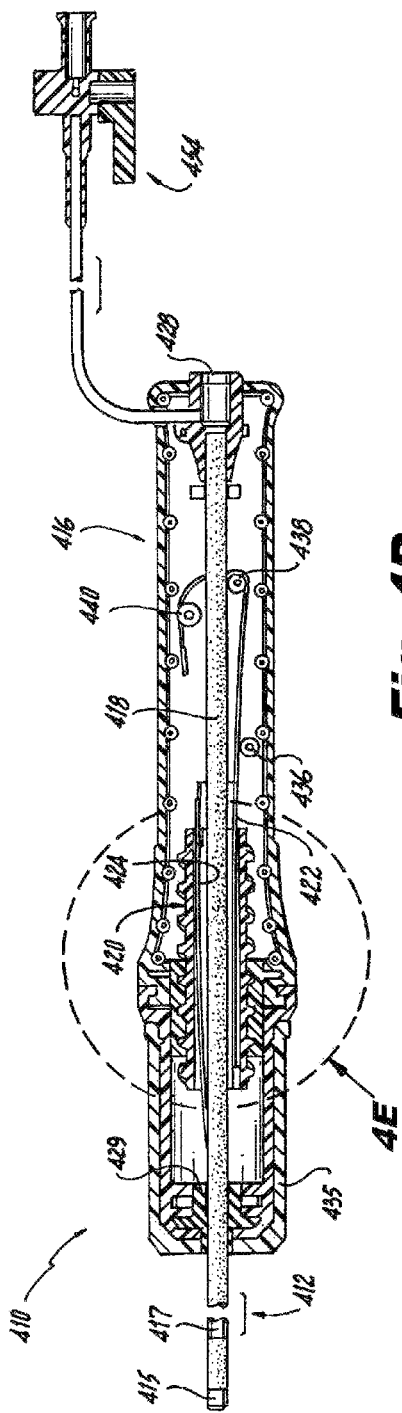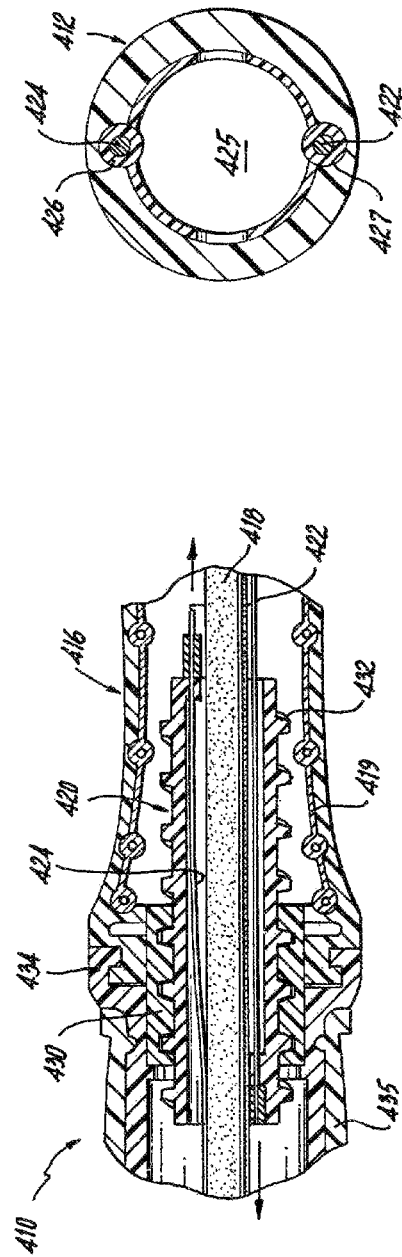
Fig. 4D
Fig. 4E
Fig. 4F

STEERABLE ABLATION CATHETER FOR RENAL DENERVATION

CROSS-REFERENCE TO RELATED APPLICATIONS

This application claims the benefit of and priority to U.S. Provisional Application No. 61/886,117, filed Oct. 3, 2013, U.S. Provisional Application No. 61/869,140, filed Aug. 23, 2013, and U.S. Provisional Application No. 61/886,132, filed Oct. 3, 2013, the contents of each being incorporated by reference herein in their entirety.

BACKGROUND OF THE INVENTION

1. Field of the Invention

The subject invention relates to ablation catheters, and more particularly, to a small diameter steerable ablation catheter for performing renal denervation procedures through the renal artery of a patient.

2. Description of Related Art

Renal denervation is a minimally invasive, endovascular catheter based procedure using radiofrequency ablation aimed at treating resistant hypertension caused by narrowing of one or both renal arteries. By applying radiofrequency pulses to the renal arteries, the nerves in the vascular wall (adventitia layer) can be denervated. This causes reduction of renal sympathetic afferent and efferent activity and decreased blood pressure.

Generally, ablating the renal artery is done by heat through radiofrequency (RF) ablation, microwave ablation, irrigated heat ablation or cryoablation. The ablation of the renal artery is commonly performed through the femoral vein, which can cause substantial bleeding. Other options include access through the renal artery, which limits the diameter of the catheter systems.

Currently ablation catheters offered are either unipolar, which take substantial time to perform effective ablation of the renal artery, or are cage form catheters, which have several electrodes configured in a cage form, or are multiple ablation electrodes configured on an inflatable balloon.

All current multi-electrode systems, therefore, have a certain disadvantage in that they are relatively large in diameter (7 F or larger) and are often difficult to position in the renal artery, requiring the use of a fixed curve or steerable renal denervation catheter. The combination of the larger catheter diameter plus the use of a renal denervation catheter results in a system that is approximately 8 F or larger. Such large diameters are not desirable for either femoral placement due to large bleeding and recovery times or renal placement.

Such conventional methods and systems have generally been considered satisfactory for their intended purpose. However, there is still a need in the art for a catheter-based ablation system that allows for improved access through the renal artery. There also remains a need in the art for such a system that is easy to make and use. The present disclosure provides a solution for these problems.

SUMMARY

In at least one aspect of this disclosure, a catheter for ablation of the interior walls of the renal artery includes an elongated catheter body having opposing proximal and distal end portions, a plurality of axially spaced apart electrodes aligned along the distal end portion of the catheter body, and a catheter handle at the proximal end portion of the catheter body including means for operatively connecting the handle to a generator, wherein energy from the generator is provided to the plurality of electrodes for ablation of the renal artery, wherein the handle is configured to steer the distal end portion of the catheter body in at least one direction. The catheter handle can include actuation means for facilitating bidirectional steering of the distal end portion of the catheter body within the renal artery.

The distal end portion can be configured to move between a first state having a generally non-linear configuration and a second state having a generally linear configuration, wherein the linear configuration of the catheter body facilitates the insertion and/or removal thereof into the renal artery.

An overall diameter of the catheter body can be about 1.67 mm or less. In some embodiments, an overall diameter of the catheter body can be 5 F or less.

A central lumen can extend through the catheter body for accommodating a stylet or guide wire used to transition the distal end portion of the catheter body between the first and second states.

The distal end portion of the catheter body can be in the second state once the stylet or guide wire is advanced through the central lumen and the distal end portion of the catheter body returns to the first state once the stylet or guide wire is removed from the central lumen.

The distal end portion of the catheter body can have a generally S-shaped configuration when it is in the first state. In other embodiments, the distal end portion of the catheter body can have a generally spiral shaped configuration when it is in the first state.

At least one thermocouple can be disposed on the distal end portion of the catheter body for regulating temperature of the plurality of electrodes during controlled ablation.

The catheter can further include a radio frequency generator operatively connected to the catheter handle to provide energy to the plurality of electrodes for ablation of the renal artery.

The catheter body can include a soft atraumatic tip portion. The tip portion of the catheter body can also include a radiopaque marker band. An infusion port can be operatively associated with the proximal portion of the catheter body for communicating fluidly with apertures provided in the distal end portion of the elongated catheter body. The catheter body can include a hydrophobic coating on an outside thereof.

In at least one aspect of this disclosure, a method for performing renal denervation on a patient includes the steps of providing an ablation catheter for insertion into the renal artery of the patient, the catheter having an elongated catheter body with opposing proximal and distal end portions, a plurality of axially spaced apart electrodes along the distal end portion of the catheter body and a catheter handle at the proximal end portion of the catheter body operatively connected to a radio frequency generator, advancing a guidewire into a central lumen of the catheter body such that the distal end portion of the catheter body is in a generally linear configuration, steering the catheter body into the renal artery of the patient, removing the guidewire such that the distal end portion of the catheter body moves into a generally non-linear configuration, and stimulating the renal arteries of the patient by energizing at least one of the plurality of electrodes.

The method can further include the steps of controlling the temperature of the distal end portion during the ablation process using at least one thermocouple disposed thereon.

BRIEF DESCRIPTION OF THE DRAWINGS

So that those skilled in the art to which the subject invention appertains will readily understand how to make and use the subject invention without undue experimentation, reference may be had to the figures, wherein:

FIG. 1A is an illustration of an embodiment of a bi-directional steerable renal denervation catheter in accordance with this disclosure, adapted for the introduction and placement of diagnostic and therapeutic devices into the human vasculature, e.g., intracardiac and transseptal placement;

FIG. 1A1 is a perspective elevational view of the steerable renal denervation catheter of the subject invention, with the distal end portion thereof arranged in an unstressed preformed undulating state;

FIG. 1A2 is a perspective elevational view of the steerable renal denervation catheter of the subject invention, with the distal end portion thereof in a stressed linear state as a result of having a stylet or guidewire extending through a central lumen thereof so that it can be readily introduced into the renal artery of a patient, wherein the distal tip is shown in a steered state;

FIG. 1B is an enlarged illustration of a lockable actuation mechanism disposed on the handle portion of the catheter body of FIG. 1A;

FIG. 1C is an illustration of a section of the catheter body of FIG. 1A, showing the outer surface of the catheter body including a hydrophobic coating;

FIG. 1D is an illustration of a cross-section of the catheter body of FIG. 1A, showing a braided interior shaft portion of the catheter body;

FIG. 1E is an illustration of an embodiment of a soft atraumatic tip portion of the catheter body of FIG. 1A, shown including two side holes for irrigation and electrodes;

FIG. 1F is an illustration of an embodiment of a hemostatic seal at the proximal end of the ergonomic handle assembly of the steerable renal denervation catheter shown in FIG. 1A;

FIG. 1G is an illustration of an embodiment of a flexible dilator that can be used in conjunction with the steerable renal denervation catheter of FIG. 1A;

FIG. 1H is an illustration of an embodiment of a French size and guide wire indicator on the proximal end of the dilator of FIG. 1G;

FIG. 1I is an illustration of depth markings presented on the dilator of FIG. 1G;

FIG. 1J is an illustration of an embodiment of a kit containing the steerable renal denervation catheter of FIG. 1A, the dilator of FIG. 1G, and a guide wire;

FIG. 1K is a top plan view of the steerable renal denervation catheter of FIG. 1A, shown including an infusion port and associated tubing;

FIG. 1L is a bottom plan view of the steerable guide catheter body of FIG. 1A;

FIG. 1M is a side elevational view of the catheter body of FIG. 1A, with the steering wires shown entering a proximal portion thereof;

FIG. 1N1 is a cross-sectional view of an embodiment of the catheter body shown in FIG. 1M taken along line 1N1-1N1;

FIG. 1N2 is a cross-sectional view of another embodiment of the catheter body shown in FIG. 1M taken along line 1N1-1N1, showing including reinforcing wires disposed within the outer catheter body;

FIG. 1O is a cross-sectional view of the catheter body shown in FIG. 1M taken along line 1O-1O;

FIG. 1P is a cross-sectional view of the handle portion of the steerable guide catheter body, with reference to FIG. 1L;

FIG. 1Q is a side, elevational view of the catheter body of FIG. 1A, shown with an embodiment of an over molded hub that supports a hemostatic seal, e.g., as shown in FIG. 1F;

FIG. 1R is a longitudinal cross-sectional view of the catheter body of FIG. 1Q, illustrating the various internal structures, steering wires, and at least one electrical wire connectable to a generator;

FIG. 2A is a side elevational view of the handle of the steerable renal denervation catheter of FIG. 1A;

FIG. 3A is a depiction of the bi-directional steerable renal denervation catheter of FIG. 1A shown having the distal end portion of the dilator body in a straight condition;

FIG. 3B is a depiction of the bi-directional steerable renal denervation catheter of FIG. 3A shown having the distal end portion of the dilator body in a first deflected position;

FIG. 3C is a depiction of the bi-directional steerable renal denervation catheter of FIG. 3A shown having the distal end portion of the dilator body in a second deflected position;

FIGS. 4B-4D illustrate aspects of the handle assembly of the steerable renal denervation catheter of FIG. 4A;

FIG. 4E is an enlarged partial cross-sectional view of the handle assembly shown in FIG. 4D, illustrating the internal components of the actuation assembly that activates the two steering wires which control the bi-directional movement of the distal end portion of the catheter body;

FIG. 4F is a cross-sectional view of the catheter body of FIG. 4A, illustrating the central lumen and opposed passages that accommodate the two steering wires;

ENABLING DESCRIPTION OF THE INVENTION

Figure 2B:
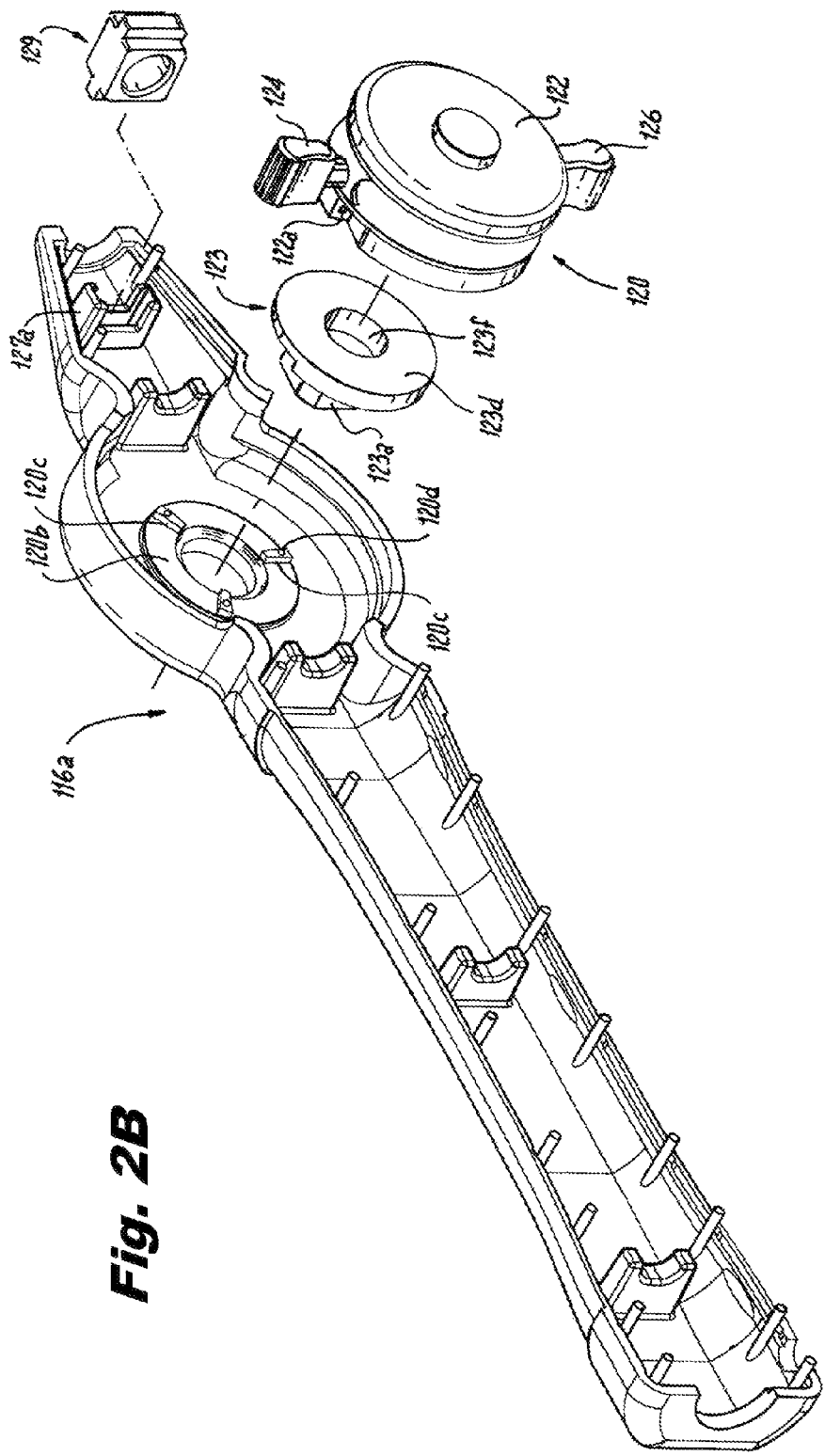
FIG. 2B is a perspective exploded view of a first half of the handle of FIG. 2A showing an actuation mechanism and other internal components relative to a first half of the handle housing.

Referring now to the drawings wherein like reference numerals identify similar structural features or elements of the disclosed devices, embodiments of this disclosure are directed to renal denervation catheters including a catheter body and handle assemblies for steering said catheter body. More particularly, the catheter 110 is adapted and configured for ablating the interior walls of the renal artery to reduce renal sympathetic afferent and efferent activity, among other things.

In at least one aspect of this disclosure, referring generally to FIGS. 1A-2N, the renal denervation catheter 110 can include an elongated catheter body 112 having a deflectable distal end portion 114. The catheter body 112 can include and/or define a central lumen 125 and a pair of diametrically opposed lateral passages 144, 146 to accommodate a corresponding pair of steering cables 134, 136. While the embodiment of FIG. 1A is shown as having two lateral passages 144, 146 and two steering cables 134, 136, any suitable number of passages and/or cables are contemplated herein, e.g., one, two, three, four, or more.

The catheter body 112 can have any suitable outer diameter size for a desired use. In some embodiments, the outer diameter size of the catheter body 112 ranges from about 4 F to about 18 F. In some embodiments, the outer diameter of the catheter body 112 is about 5 F. In other embodiments, the diameter of the catheter body 112 is about 1.67 mm or less.

The proximal end portion 118 of the catheter body 112 can extend through the steering handle 116 to a proximal end thereof. A hemostatic seal 128 can be operatively associated with the proximal end portion 118 of the catheter body 112 such that the hemostatic seal 128 is in fluid communication with the central lumen 125 thereof. In at least some embodiments, the hemostatic seal 128 can provide an effective seal for a guide wire of about 0.014 inches.

The catheter body 112 can have a hydrophobic coating or any other suitable and/or desired coating. In some embodiments, the catheter body 112 can be formed from a hydrophobic material.

The catheter body 112 can include a multi-layer structure at one or more portions thereof. Referring to FIGS. 1D and 1N1, a portion of the catheter body 112 can include one or more of an outer layer 112a, a secondary layer 112b, a braided layer 112c, and/or an internal layer forming a central lumen 112d. The outer layer 112a, the secondary layer 112b, and the internal layer 112d can include any suitable flexible material, e.g., a biocompatible plastic, metal, or the like. The braided layer 112c can include any suitable braided structure made up of strands of any suitable material (e.g., biocompatible plastic, fabric, metal). In some embodiments, the braided layer 112 is formed into the one or more of the outer layer 112a and/or the secondary layer 112b such that the outer layer 112a and/or secondary layer 112b have braiding or mesh included therein (e.g., via over molding biocompatible plastic on a braded/mesh tubing).

Alternatively, referring to FIG. 1N2, the catheter body 112 can include reinforcing wires 111 disposed within the outer catheter body 112a. The reinforcing wires 111 can be made of any suitable material (e.g., metal) and may be configured for a specific rigidity. The reinforcing wires 111 may be configured as a mesh layer molded into the outer layer 112a.

Using such designs as shown in FIGS. 1N1 and 1N2 can allow the flexibility of catheter body 112 to be controlled. In some embodiments, the flexibility of the catheter body 112 can be modified as a function of length of the catheter body 112 to control the point along the catheter body 112 that the distal portion deflects about and/or degrees of deflection of portions of the catheter body 112.

As shown in FIG. 1O, such a multi-layer structure may comprise only a portion of the catheter body 112, and another portion of the catheter body 112 (e.g., a proximal portion within the handle) can include only an outer layer 112a. Any other suitable configuration for catheter body layering or catheter body design is contemplated herein.

Referring specifically to FIGS. 1A, 1M, 1Q, and 1R, the catheter body 112 can also include a soft atraumatic tip portion 115 disposed on the distal end thereof. In some embodiments, the tip portion 115 can include one or more side holes 115a, 115b in fluid communication with an infusion port 154 (e.g., including a conventional leur fitting) associated with the steering handle 116. As shown in FIG. 1E, the tip portion 115 can include an opening 115c in fluid communication with the central lumen 125.

The distal end portion 114 can also include a radiopaque marker 113b. The radiopaque marker 113b can be any suitable shape (e.g., a cylinder) and can include any radiopaque material and/or the like for locating the radiopaque marker 113b in situ to enable the visual guidance of the catheter body 110 through the vascular system of a patient using a suitable imaging system.

The distal end portion 114 can also include and anchor member 113a disposed therein configured to anchor the steering wires 134, 136 to the distal end portion 114. The anchor member 113a can be of any suitable shape (e.g., cylindrical) and mounted within the distal end portion 114 of the catheter body 112 such that the anchor member 113a does not move relative to the distal tip when pulled on by the steering wires 134, 136.

Referring additionally to FIGS. 1A1 and 1A2, the distal end portion 114 of the catheter body 112 can be adapted and configured to move between a first state or condition having a generally non-linear configuration (e.g., unstressed undulating configuration of FIG. 1A1), and a second state or condition having a substantially linear configuration (e.g., as shown in FIG. 1A2). The linear configuration of the second state facilitates the insertion and/or removal of the catheter body 112 into a renal artery or other suitable location.

A stylet or guidewire can be used to effectuate the transition of the catheter body 112 from the non-linear configuration shown in FIG. 1A1 to the linear configuration shown in FIG. 1A2. For example, the catheter body 112 can have the undulating shape of FIG. 1A1 in an unstressed configuration but can be made to be more linear with the insertion of dilator 170. As shown in FIG. 1A2, it is contemplated that, in embodiments, the catheter body 112 can still be steered even when a dilator 170 is inserted therein. The concept of moving a preformed catheter body between a preformed (unstressed) condition and linear (stressed) condition has been shown and described with respect to an epidural neurostimulation lead in U.S. Patent Application Publication 2006/0041295 to Osypka, the disclosure of which is herein incorporated by reference in its entirety.

A plurality of axially spaced apart electrodes 117 is disposed along the distal end portion of the catheter body 112 and can be configured for any suitable electrosurgical procedure. The electrodes 117 can be electrically connected to one another and to the catheter handle 116 by at least one conductive wire 117a (e.g., as shown in FIG. 1R). It is contemplated that the soft atraumatic tip 115 can also be made of a soft conductive material to act as an electrode 117 or can be any suitable electrode instead of being soft.

The proximal end of catheter handle 116 can include any suitable electrical connector in electrical communication with wire 117a and electrodes 117. The connector can be operatively connectable to a radio frequency (RF) generator or other suitable electrosurgical generator. In this regard, energy from the RF generator is delivered through conductive wires (not shown) to the plurality of electrodes 117 on the distal end portion of catheter body 112 to facilitate localized and directed ablation of specific locations on the interior wall of the renal artery or other suitable location. The connector at the proximal end of catheter handle 116 can also be included in the hemostatic seal such that the connector can also act as the entry point for introducing a guidewire or stylet into the central lumen of the catheter body 112.

It is envisioned that at least one thermocouple can be disposed along the distal end portion 114 of the catheter body 112 to regulate temperature of the plurality of electrodes 117 for controlled ablation.

In embodiments, the distal end portion 114 of the catheter body 112 can include a generally S-shaped configuration in the unstressed first state as shown in FIG. 1A1. In this condition, the distal end portion 114 of the catheter body 112 is positioned generally within one geometric plane.

Figure 5A:
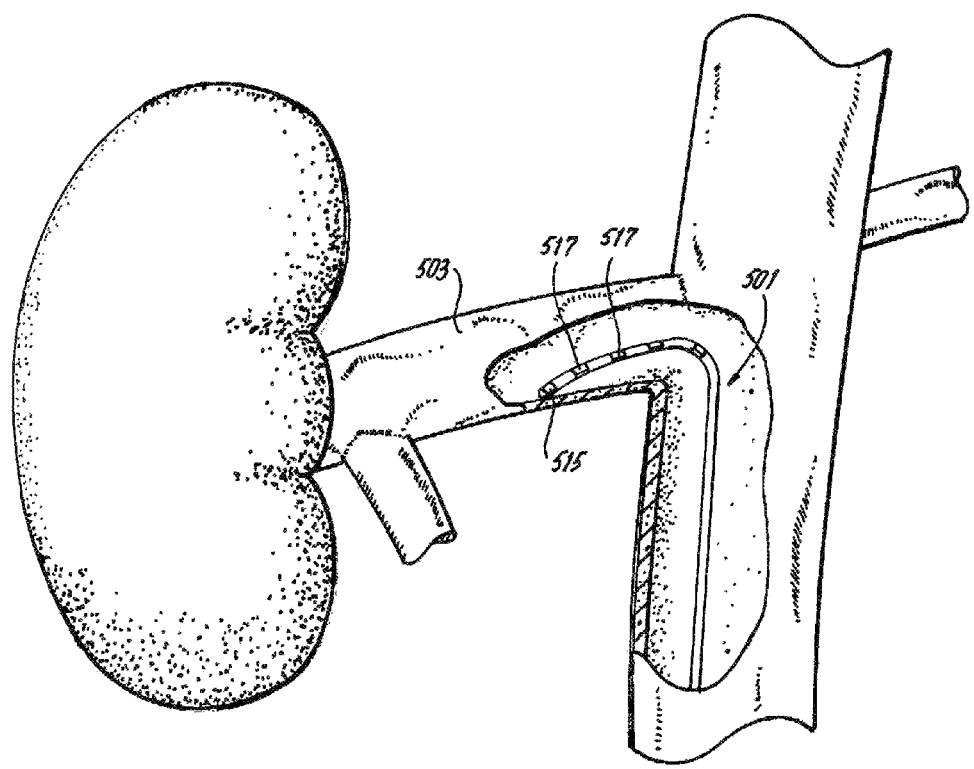
FIG. 5A is an in-situ view of an embodiment of this disclosure disposed within a renal artery during a medical procedure, showing a substantially linear distal end portion.
Figure 5B:
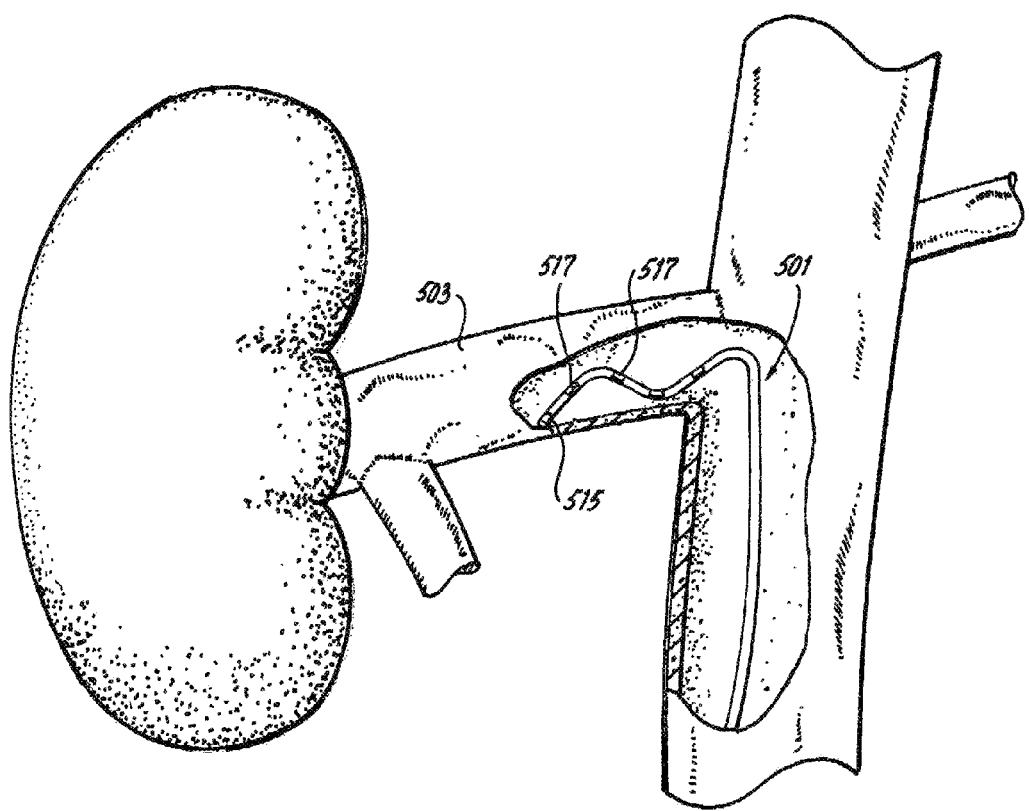
FIG. 5B is an in-situ view of an embodiment of this disclosure disposed within a renal artery during a medical procedure showing an undulating distal end portion.
Figure 5C:
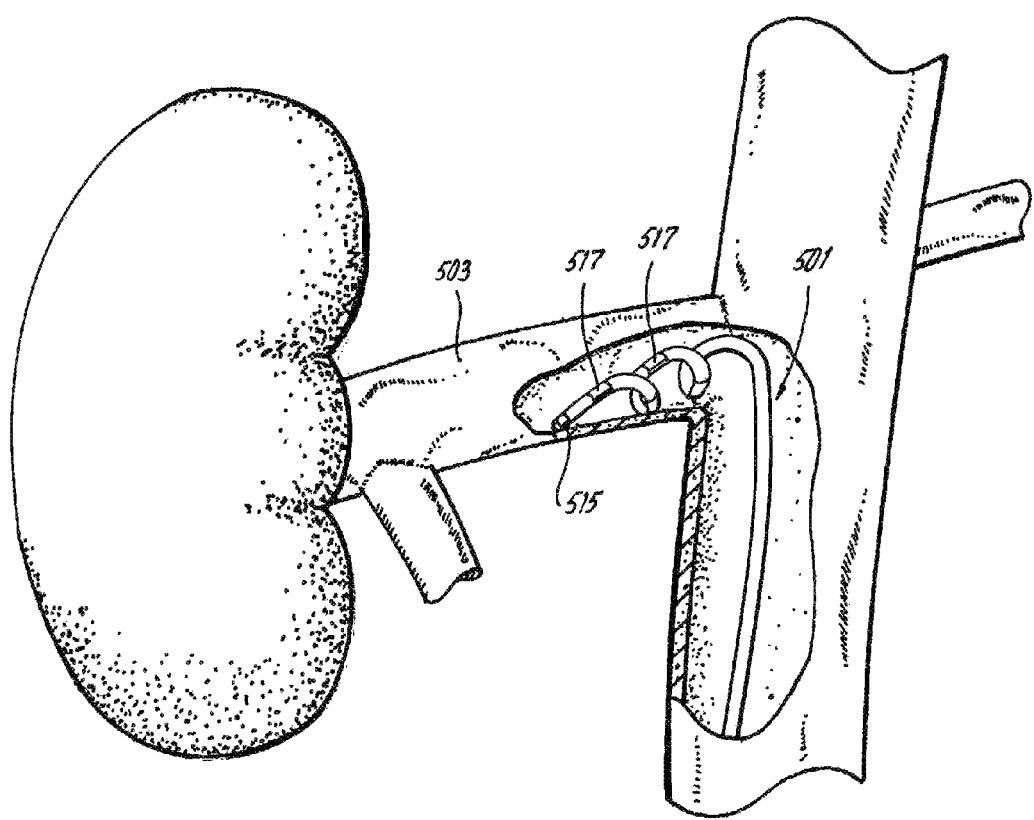
FIG. 5C is an in-situ view of an embodiment of this disclosure disposed within a renal artery during a medical procedure showing a spiral distal end portion.

In an alternate embodiment, the distal end portion 114 of the catheter body 112 can include a generally spiral shaped configuration in the unstressed state, as shown for example in situ in FIG. 5C. In this condition, the distal end portion 114 of the catheter body 112 exists in three dimensional planes.

The steerable renal denervation catheter 110 further includes a steering handle 116 operatively associated with a proximal end portion 118 of the catheter body 112 and an actuation mechanism 120 that is operatively connected to the pair of steering cables 134, 136 accommodated within the opposed lateral passages 144, 146 of the catheter body 112 for steering the deflectable distal end portion 114 of the catheter body 112 in one or more directions (e.g., bi-directionally as shown in this embodiment).

Figure 2C:
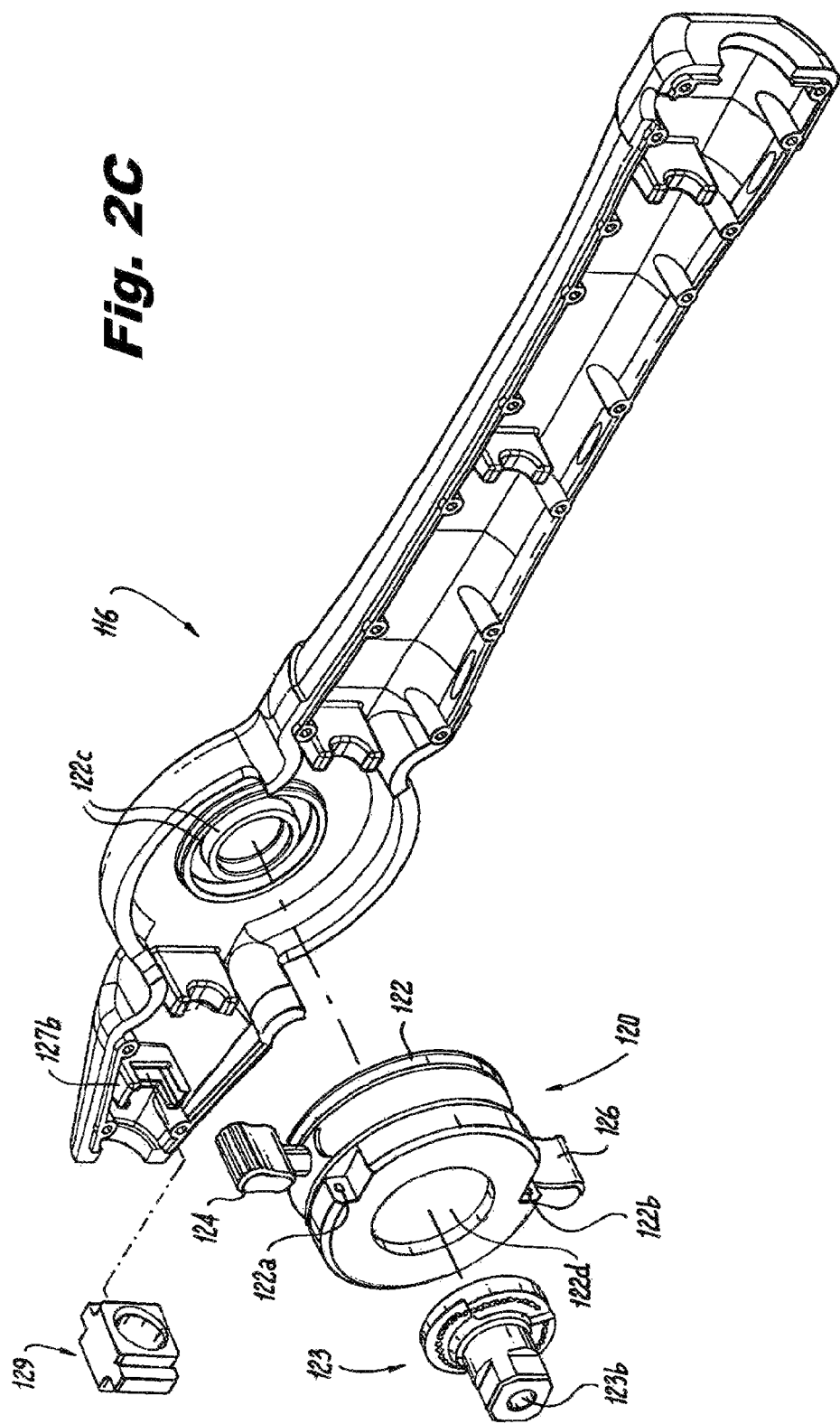
FIG. 2C is a perspective exploded view of a second half of the handle of FIG. 2A showing an actuation mechanism and other internal components relative to a second half of the handle housing.
Figure 2D:
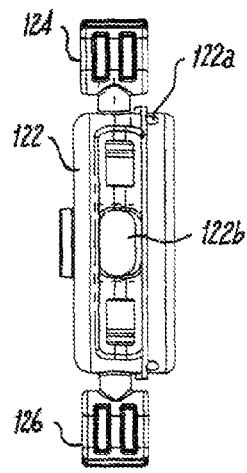
FIG. 2D is a front view of the actuation mechanism of FIGS. 2B and 2C.
Figure 2E:
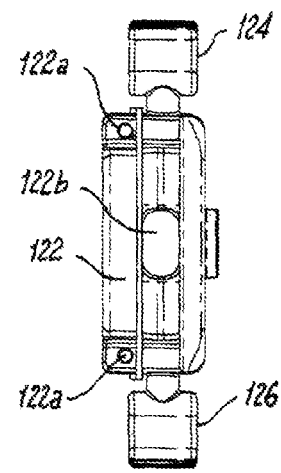
FIG. 2E is a rear view of the actuation mechanism of FIGS. 2B and 2C.
Figure 2F:
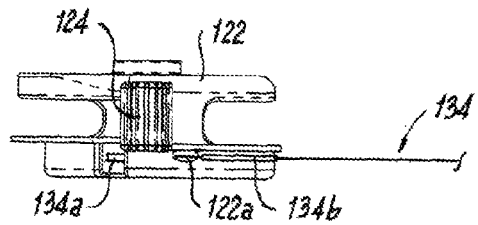
FIG. 2F is a side view of the actuation mechanism of FIGS. 2B and 2C.

Referring to FIG. 2A-2C, a first half 116a of the handle 116 includes lock surface 120b on the inside portion of the first half 116a defining an opening between the inside of the handle 116 and the outside thereof. The lock surface 120b includes one or more cam protrusions 120c extending from the lock surface 120b. The cam protrusions 120c include one or more lock protrusion 120d. The cam protrusions 120c are configured to engage a friction lock member 123 described in more detail below.

As shown in FIGS. 2B and 2C, the first and second halves 116a, 116b are dimensioned to accept the actuation mechanism 120 therein. As shown in FIG. 2C, the second half 116b can include ridges 122c or any other surface inside the second half 116b to allow the central hub 122 of the actuation mechanism 120 to rotate relative to the handle 116.

Referring to FIGS. 2B, 2C, and 2D-2F, the actuation mechanism 120 of the steering handle 116 can include a central hub 122 connected to the actuators 124, 126. The central hub 122 can define a passageway 122b configured to allow the catheter body 112 to pass therethrough. The passageway 122b is dimensioned to prevent bending or moving the portion of the catheter body 112 passing therethrough between the limits of actuation of the actuation mechanism 120.

The flexible steering cables 134, 136 can be secured to the periphery of the central hub 122 of actuation mechanism 120. For example, the central hub 122 can define wire holes 122a which steering cables 134, 136 can pass through. The steering cables 134, 136 can be secured to the central hub 122 using a crimp 134a or any other suitable attachment. In some embodiments, a guide member 134b can be disposed around the steering cable 134, 136 distal of the wire holes 122a to prevent the steering cables from bending around the central hub 122 allowing the steering cables 134, 136 to angle inwardly toward the catheter body 112 without bending the cables 134, 136.

Also as shown best in FIG. 2C, the central hub 122 can define a friction lock cavity 122d configured to accept a friction lock member 123 therein. As shown the actuation mechanism 120 can be a single molded piece of material (e.g., suitable plastic), but any suitable combination of parts is contemplated herein.

As shown in FIG. 2B, a friction lock member 123 is configured to be disposed between the actuation mechanism 120 and the first half 116a of the housing 116. Referring to FIG. 2I-2L, the friction lock member 123 can include a pedestal portion 123a defining a hole 123b therethrough and a flange portion 123d extending from the pedestal portion 123a. The flange portion 123d can define a frictional surface for engaging the central hub 122 of the actuation mechanism 120. In addition, the flange portion 123d includes one or more camming surfaces 123c which can define locking divots 123e. The camming surfaces 123c can include any suitable shape (e.g., ramped as shown).

Figure 2G:
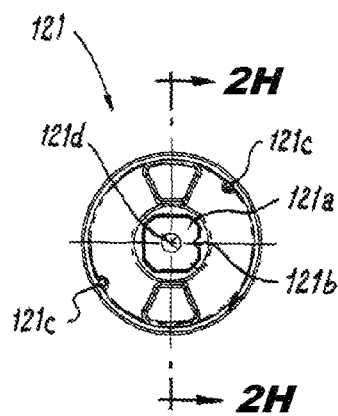
FIG. 2G is a bottom plan view of a locking tab of the locking mechanism of the device of FIG. 2A.
Figure 2H:
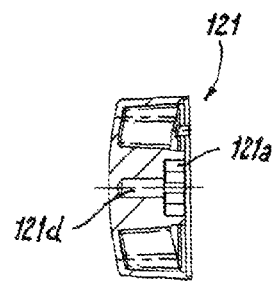
FIG. 2H is a cross-sectional side view of a locking tab of the locking mechanism of the device of FIG. 2A.
Figure 2I:
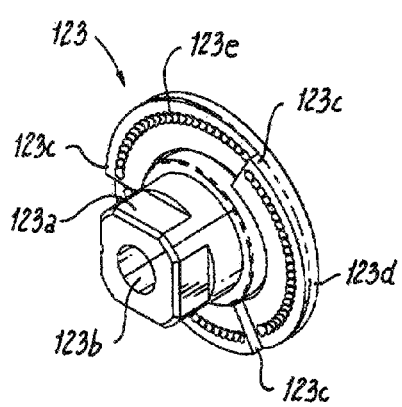
FIG. 2I is a perspective view of an embodiment of the friction lock member of FIGS. 2B and 2C, showing camming surfaces and locking divots on the camming surfaces.
Figure 2J:
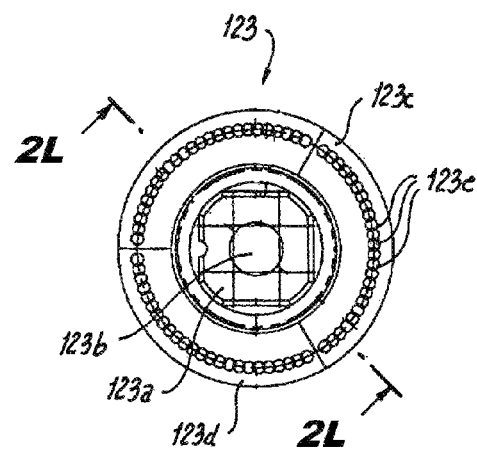
FIG. 2J is a top plan view of an embodiment of the friction lock member of FIG. 2I.
Figure 2K:
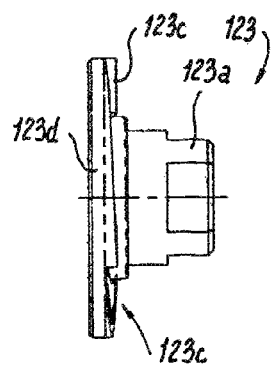
FIG. 2K is a side view of an embodiment of the friction lock member of FIG. 2I.

Referring to FIGS. 2G and 2H, a locking tab 121 of the locking mechanism 120a can include a body 121b shaped to be gripped by a user and a pedestal cavity 121a defined therein dimensioned to receive the pedestal portion 123a of the friction lock member 123. An attachment hole 121d can be included within the pedestal cavity 121a to allow a screw or other suitable member to affix thereto to attach the friction lock member 123 to the locking tab 121.

Figure 2L:
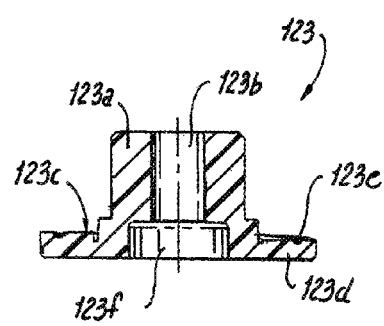
FIG. 2L is a cross-sectional side view of an embodiment of the friction lock member of FIG. 2I.

Referring additionally to FIG. 2L, an attachment member (e.g., a screw) can be passed through hole 123b and into attachment hole 121d to attach the friction lock member 123 to the locking tab 121 in a sandwich with the housing 116 therebetween. The attachment member can be dimensioned such that a head of the attachment member can seat into head cavity 123f of the and an attachment portion of the attachment member can advance into attachment hole 121d sufficiently to sufficiently sandwich the housing 116 between the locking tab 121 and the friction lock member 123 against the lock surface 120b while still allowing the assembly to rotate when the locking tab 121 is rotated.

In this regard, the cam protrusions 120c maintain contact with the camming surfaces 123c such that when the locking tab 121 is rotated, the friction lock member 123 rotates therewith causing the relative position of the cam protrusions 120c to change relative to the camming surfaces 123c. When the cam protrusions 120c are in contact with a thicker portion of the camming surfaces 123c, the friction lock mechanism 123 is moved closer to the central hub 122, causing the friction surface of the flange 123d to push upon the central hub 122 to produce more frictional resistance to rotation of the hub 122. The lock protrusions 120d mate with the locking divots 123e to prevent the locking member 123 from slipping back down the cam path and provide a tactile feedback while turning the locking tab 120a between an unlocked position and a locked position.

Any other suitable locking mechanism 120a and/or components thereof to prevent or inhibit movement of the actuators 124, 126 is contemplated herein.

Figure 2M:
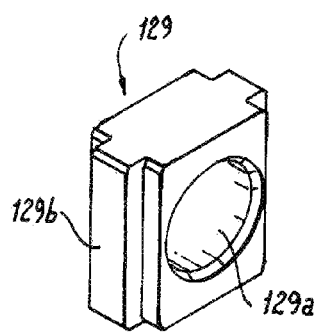
FIG. 2M is a perspective view of a catheter body stabilizing member, showing a catheter body hole and flange members extending therefrom.
Figure 2N:
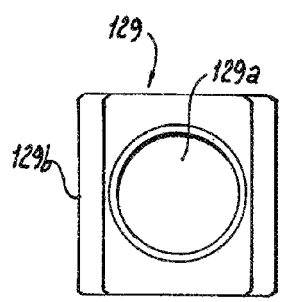
FIG. 2N is a top plan view of the catheter body stabilizing member of FIG. 2M.

Referring to FIGS. 2M and 2N in conjunction with FIGS. 2B and 2C, a catheter body stabilizing member 129 can include a catheter body hole 129a dimensioned for the catheter body to pass therethrough and flange members 129b extending therefrom. The catheter body stabilizing member 129 is configured to fit within stabilizing member holders 127a, 127b that are disposed on the inside of the first and second halves 116a, 116b, respectively. The catheter body stabilizing member 129 allows the catheter body 112 to be directed at the distal end of the handle 116 so that motion of the catheter body 112 within the handle 116 can be resisted.

When assembled and in an unlocked position, the actuation mechanism 120 can rotate between first half 116a and second half 116b of the housing 116 to steer the distal tip of the catheter body 112. The locking tab 121 can be moved between an unlocked position such that the actuation mechanism 120 can rotate without substantial resistance and a locked position such that a resistance to rotation is created by the locking mechanism 120a. Additionally, positions between the unlocked and locked position can be selected by a user such that the sensitivity of control of the distal end of the catheter body 112 is modified. In such an instance, the amount of force provided by the locking mechanism 120a can be modified by turning the locking mechanism 120a to a particular position between the locked position and the unlocked position, thereby altering the force required to deflect the distal end portion 114. This can be used to allow the user to modify the sensitivity of the actuating mechanism 120 using the locking mechanism 120a.

Referring to FIGS. 3A-3C the catheter body 112 is shown being steered from a straight position (FIG. 3A) to a first deflected position (FIG. 3B) and a second deflected position (FIG. 3C). In use, manipulation of the actuators 124 and 126 in clockwise and counter-clockwise directions causes the corresponding movement of the central hub and steering cables 134 and 136. This results in the bi-directional deflection of the distal end portion 114 of the catheter body 112. It is contemplated that clockwise actuator motion can lead to a counter-clockwise tip deflection, and vice versa. The actuation mechanism 120 controls the orientation of the distal end portion of the catheter body and can be designed to have any suitable maneuverability (e.g., 180° dual deflection maneuverability).

Referring to FIGS. 1F-1J, the steerable renal denervation catheter 110 can further include and/or be operative with a flexible dilator 170 dimensioned for introduction through the central lumen 125 of the catheter body 112 and/or the hemostatic seal 128. The dilator 170 includes a dilator shaft 171 and a dilator tip 175. In some embodiments, the dilator 170 can have an axial passage extending therethrough for accommodating a flexible guide wire 180. As shown in FIGS. 1F and 1I, in some embodiments, the dilator 170 can further include depth markings for accurate placement and/or indicia indicating French size. Indicia for indicating French size of the dilator shaft 171 can be located on a proximal portion 173 or any other suitable portion of the dilator 170.

Referring specifically to FIG. 1J, a kit 1001 for placing a surgical device in the vasculature of patient can include an enclosure (not shown), a steerable renal denervation catheter 110 disposed within the enclosure, a dilator 170 disposed within the enclosure, and a guide wire 180 disposed in the enclosure.

Figure 4A:
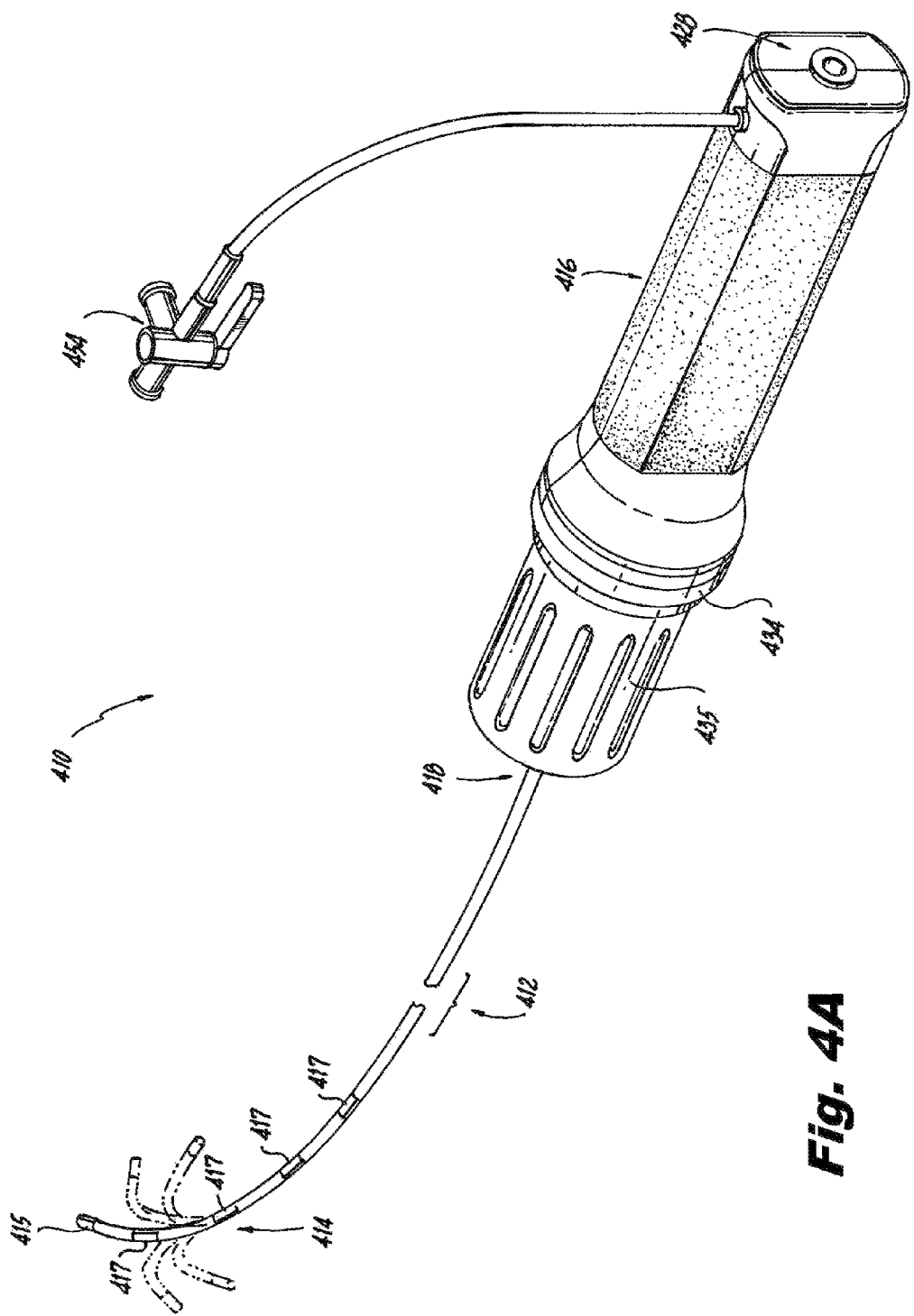
FIG. 4A is an illustration of an embodiment of a bi-directional steerable renal denervation catheter having another embodiment of a handle assembly in accordance with this present disclosure.

In at least one aspect of this disclosure, referring now to FIGS. 4A-4F, the steerable medical device can be a steerable renal denervation catheter 410 having a differing handle assembly 416 than the above described embodiments. The steerable renal denervation catheter 410 includes an elongated catheter body 412 having a deflectable distal end portion 414 and a central lumen 425 (see FIG. 4F). As shown in FIG. 4A, the distal end portion 414 of catheter body 412 can be adapted and configured to achieve about a 180 degree deflection (e.g., mono-directional, bidirectional). Other suitable maximum deflections are contemplated herein.

It is envisioned that at least one thermocouple can be disposed along the distal end portion of the catheter body 412 to regulate temperature of the plurality of electrodes 417 for controlled ablation.

Similar to the other catheter bodies described herein, the catheter body 412 can have an outer diameter size ranging from about 4 F to about 18 F. Any other suitable size is contemplated herein.

The steerable renal denervation catheter 410 includes an elongated handle assembly 416 operatively associated with a proximal end portion 418 of the catheter body 412. The proximal end portion 418 of the catheter body 412 can extend through the steering handle 416 to a proximal end thereof.

A hemostatic seal 428 can be operatively associated with the proximal end portion 418 of the catheter body 412 and in fluid communication with the central lumen 425. As disclosed above, a hemostatic seal 428 permits sealed introduction of a dilator, guide wire, or other medical device.

The catheter body 412 can include a hydrophobic coating and/or a soft atraumatic tip portion 415 similar to those as described above. The tip portion 415 of the catheter body 412 can include a radiopaque marker band similar to marker band 113b as described above. An infusion port 454 (e.g., including a conventional leur fitting) can be operatively associated with the proximal portion of the catheter body 412 for fluidly communicating with apertures (not shown) provided in the distal end portion 414 of the elongated catheter body 412.

A plurality of axially spaced apart electrodes 417 is disposed along the distal end portion of the catheter body 412 and can be configured for any suitable electrosurgical procedure. The electrodes 417 can be electrically connected to one another and to the catheter handle 416 by at least one conductive wire (e.g., similar to as shown in the embodiment of FIG. 1R). It is contemplated that the soft atraumatic tip 415 can also be made of a soft conductive material to act as an electrode 417 or can be any suitable electrode instead of being soft.

The proximal end of catheter handle 416 can include any suitable electrical connector in electrical communication with electrodes 417. The connector can be operatively connectable to a radio frequency (RF) generator or other suitable electrosurgical generator. In this regard, energy from the RF generator is delivered through conductive wires (not shown) to the plurality of electrodes 417 on the distal end portion of catheter body 412 to facilitate localized and directed ablation of specific locations on the interior wall of the renal artery or other suitable location. The connector at the proximal end of catheter handle 416 can also be included in the hemostatic seal such that the connector can also act as the entry point for introducing a guidewire or stylet into the central lumen of the catheter body 412.

The handle assembly 416 of steerable renal denervation catheter 410 includes a body 419 that houses a manually operable actuation mechanism 420. The actuation mechanism 420 can be operatively connected to one or more steering wires 422 and 424. As best seen in FIG. 4F, the steering wires 422 and 424 can be accommodated within opposed lateral passages 426 and 427 of the catheter body 412. As shown in this embodiment, the steering wires 422 and 424 are arranged to control the deflection of the distal end portion 414 of the catheter body 412 in two directions, as described in more detail herein below.

As best seen in FIG. 4E, the actuation mechanism 420 can include a drive nut 430 that is threadably coupled to a worm coil 432. Rotation of the drive nut 430 causes axial translation of the worm coil 432 within the body 419 of the handle assembly 416. The drive nut 430 and worm coil 432 can include a common thread pitch that is selected to achieve a precise amount of control over the deflection achieved at the distal end portion 414 of the catheter body 412. For example, differing thread pitches advance the worm coil 432 at different rates, allowing more or less motion of the tip relative to the amount of motion of the user, thereby modifying precision. It would be appreciated by those having skill in the art that the more control a surgeon has over the deflection of the distal end of the catheter body, the easier it is for that surgeon to accurately steer the catheter body 412 though the vasculature of a patient to the site of a procedure.

The actuation mechanism 420 further includes a manually rotatable torque ring 434 that is operatively connected to the drive nut 430 and configured to be rotated by a user. The torque ring 434 can be positioned adjacent a stationary torque grip 435, thereby enabling a user to maintain a firm grip on the device 410 while rotating the torque ring 434 to achieve the directional deflection of the distal end portion 414 of the catheter body 412. As shown, the steering wire 422 can be operatively connected or otherwise crimped to a distal end portion of the worm coil 432 of actuation mechanism 420. Also as shown, the other steering wire 424 can be operatively connected or otherwise crimped to a proximal end portion of the worm coil 432. As best seen in FIG. 4D, steering wire 422 can be longer than the steering wire 424.

The longer steering wire 422 can be operatively supported by a pair of guide rollers 436 and 438. Guide roller 436 can be disposed in a stationary position within the body 419 of handle assembly 416. In contrast, guide roller 438 can be dynamically positioned within the body 419 of handle assembly 416, such that the guide roller 438 is operatively associated with a spring biased tension arm 440 that is pivotally mounted within the body 419 of handle assembly 416. As shown in FIG. 4D, the steering wire 422 can be looped around the dynamic guide roller 438 so that it doubles back around toward the crimped end of the wire and then out to the distal end portion 414 of the catheter body 412.

In operation, when the worm coil 432 translates in a distal direction through rotation of drive nut 430, the end of the longer steering wire 422 that is crimped to the distal end portion of the worm coil 432 is pulled in a distal direction. Consequently, the portion of steering wire 422 that double backs around guide roller 438 is pulled in a proximal direction. This causes controlled deflection of the distal end portion 414 of the catheter body 412.

When the worm coil 432 translates in a proximal direction through the reverse rotation of drive nut 430, the shorter steering wire 424 that is crimped to the proximal end portion of worm coil 432 is pulled in a proximal direction therewith. This causes controlled deflection of the distal end portion 414 of catheter body 412 in an opposite direction. At the same time, the crimped end of the longer steering wire 422 moves proximally with the worm coil 432, and the slack in that wire is accommodated by the spring biased tension arm 440.

The actuation mechanism 420 and the arrangement of steering wires 422, 424 allows for the bidirectional deflection of the distal end portion 414 of the catheter body 412 using a worm coil 432 that has a single uniform thread pitch. Those skilled in the art will readily appreciate that the amount or degree of deflection, and the associated precision steering that can be achieved, can be adjusted by changing the thread pitch of the drive nut 430 and worm coil 432 as described above. That is, a greater amount of precision for the deflection of the distal end portion 414 of catheter body 412 can be achieved by increasing the thread pitch of the drive nut 430 and worm coil 432.

While embodiments of steerable ablation devices have been described above, it is also contemplated that the device need not be steerable, but merely transitionable between first and second states. It is also contemplated that devices herein need not include a steering handle. Any other suitable handle is contemplated herein.

In at least one aspect of this disclosure, a method for performing renal denervation on a patient includes the step of providing an ablation catheter 110, as disclosed herein, dimensioned and configured for insertion into the renal artery of a patient. The method can further include one or more of the steps including advancing a guidewire within a central lumen of the catheter body 112 such that the distal end portion thereof is in a linear configuration, inserting the catheter body 112 through the renal artery of the patient, and removing the guidewire such that the distal end portion 114 of the catheter body 112 moves into an unstressed non-linear or undulating configuration. The method can further include the steps of energizing at least one of the plurality of electrodes 117, and controlling or otherwise monitoring the temperature of the distal end portion 114 of the catheter body 112 during the ablation process using at least one thermocouple disposed thereon.

FIGS. 5A-5C show embodiments of a steerable device 501 having electrodes 517 and a distal tip 515 in situ in a renal artery 503 of a patient. FIG. 5A shows a linear state, 5B shows an undulating state, and FIG. 5C shows a spiral state.

The devices, methods, and systems of the present disclosure, as described above and shown in the drawings, provide for steerable medical devices with superior properties including advanced directional and precision control. While the apparatus and methods of the subject disclosure have been shown and described with reference to embodiments, those skilled in the art will readily appreciate that changes and/or modifications may be made thereto without departing from the spirit and scope of the subject disclosure.

What is claimed is:

1. A catheter for ablation of the interior walls of the renal artery, comprising:
   a) an elongated catheter body having opposing proximal and distal end portions and having a central lumen extending therethrough, wherein the distal end portion of the catheter body is deflectable;
   b) a plurality of axially spaced apart ablation electrodes aligned along the distal end portion of the catheter body, wherein the distal end portion of the catheter body is configured to move between a first state having a preformed generally non-linear configuration to facilitate ablation of the renal artery by the ablation electrodes and a second state having a generally linear configuration to facilitate insertion of the distal end portion of the catheter body into the renal artery;

c) an elongated catheter handle at the proximal end portion of the catheter body having a longitudinal axis and including at least one conductive wire operatively connecting the catheter handle to a generator, wherein energy from the generator is provided to the plurality of ablation electrodes through the at least one conductive wire for ablation of the renal artery, wherein the catheter handle includes a manually controlled actuation assembly including a pair of steering cables for facilitating bidirectional steering of the deflectable distal end portion of the catheter body within the renal artery, and wherein the manually controlled actuation assembly is supported within a cavity of the catheter handle, the cavity having an annular lock surface that includes one or more lock protrusions, and wherein the actuation assembly includes:

a central hub operatively connected to the pair of steering cables and mounted for rotation within the cavity of the catheter handle about an axis that extends perpendicular to the longitudinal axis of the catheter handle, wherein the central hub includes an axial friction lock cavity; and a friction lock member coaxially positioned within the axial friction lock cavity of the central hub, wherein the friction lock member includes at least one camming surface engaged with the central hub to provide variable frictional resistance to relative rotation of the central hub, wherein locking divots are defined in the at least one camming surface of the friction lock member for mating with the one or more lock protrusions on the annular lock surface of the cavity of the catheter handle to prevent the friction lock member from slipping and to provide tactile feedback to a user when the friction lock member is rotated; and d) an elongated flexible dilator configured to facilitate movement of the distal end portion of the catheter body between the first and second states, wherein the distal end portion of the catheter is in the first state when the dilator is removed from the central lumen of the body and the distal end portion of the catheter body is in the second state when the dilator is inserted though the central lumen of the body into the distal end portion of the catheter body, and wherein the distal end portion of the catheter body can be steered by the manually controlled actuation assembly even when the flexible dilator is inserted therein to maintain the distal end portion in the second state.

2. The catheter as recited in claim 1, wherein the distal end portion of the catheter body has a generally undulating configuration when it is in the first state.

3. The catheter as recited in claim 1, wherein the distal end portion of the catheter body has a generally spiral shaped configuration when it is in the first state.

4. The catheter as recited in claim 1, wherein at least one thermocouple is disposed on the distal end portion of the catheter body for regulating temperature of the plurality of electrodes during controlled ablation.

5. The catheter as recited in claim 1, wherein an overall diameter of the catheter body is 5 F or less.

6. The catheter as recited in claim 1, wherein the catheter body includes a soft atraumatic tip portion.

7. The catheter as recited in claim 6, wherein the tip portion of the catheter body includes a radiopaque marker band.

8. The catheter as recited in claim 1, wherein an infusion port is operatively associated with the proximal portion of the catheter body for communicating fluidly with apertures provided in the distal end portion of the elongated catheter body.

9. The catheter as recited in claim 1, wherein the catheter body includes a hydrophobic coating on an outside thereof.

10. The catheter as recited in claim 1, wherein the elongated flexible dilator includes an elongated dilator shaft having a tapered distal tip portion and a proximal portion, and wherein depth markings are provided along the proximal portion of the elongated dilator shaft for accurate placement.

11. The catheter as recited in claim 10, wherein the elongated flexible dilator includes indicia along the proximal portion of the elongated dilator shaft for indicating a French size of the elongated dilator shaft.

12. The catheter as recited in claim 10, further comprising a flexible guide wire, and wherein the elongated flexible dilator has an axial passage for accommodating the flexible guide wire.

13. The catheter as recited in claim 1, wherein the catheter body has a multi-layered construction including an outer layer, a braided layer and an internal layer forming the central lumen.

* * * * *